United States Patent [19]

Terasaki et al.

[11] Patent Number: 4,752,569

[45] Date of Patent: Jun. 21, 1988

[54] SIALYLATED LEWIS$^x$ EPITOPE, ANTIBODIES AND DIAGNOSIS

[75] Inventors: Paul I. Terasaki, Los Angeles; Masaki Hirota; Kiyoyasu Fukushima, both of Gardena; Akemi Wakisaka; Takashi Iguro, both of Torrance, all of Calif.

[73] Assignee: The Regents of the University of California, Berkeley, Calif.

[21] Appl. No.: 623,309

[22] Filed: Jun. 21, 1984

[51] Int. Cl.$^4$ .................. C12N 5/00; C12N 15/00; G01N 33/532; G01N 33/574
[52] U.S. Cl. ......................... 435/7; 435/172.2; 435/240.27; 436/544; 436/548; 436/813; 530/387; 530/389; 530/808; 935/104; 935/110
[58] Field of Search ............... 435/240, 948, 172.2, 435/7; 436/520, 527, 544, 545, 546, 548, 813, 822, 64; 935/106, 108, 110, 104; 260/112 B, 112 R; 530/389, 808, 809, 387

[56] References Cited

PUBLICATIONS

T. M. Kloppel et al. *Proc. Nat. Acad. Sci.* (USA) 74 3011, 1977.
G. Köhler et al. *Nature* (London) 256 495, 1975.
K. Y. Pak et al. *Hybridoma* 3 1, 1984.
M. Blaszczyk et al. Int. Journ. Cancer 33, 313–318, 1984.

*Primary Examiner*—Sidney Marantz
*Assistant Examiner*—David A. Saunders
*Attorney, Agent, or Firm*—Bertram I. Rowland

[57] ABSTRACT

Detection of sialylated Lewis$^x$ antigen in sera is employed as diagnostic of the presence of cancer. Conveniently, monoclonal antibodies are provided which are shown to be useful in the diagnosis of a neoplastic condition, with a wide variety of different tumors.

The hybridoma CSLEX1 was deposited at the A.T.C.C. on June 20, 1984 and given Accession No. HB8580.

11 Claims, No Drawings

SIALYLATED LEWIS$^x$ EPITOPE, ANTIBODIES AND DIAGNOSIS

BACKGROUND OF THE INVENTION

1. Field of the Invention

There have been numerous reports of monoclonal antibodies directed to tumor associated antigens. However, only a few of these have been found useful to detect tumor associated antigens in sera. For the most part, where an antigen has been found to be associated with neoplastic tissue, but not with adjacent normal tissue, it has subsequently been found that the antigen is present in normal tissue at other sites. Therefore, in many instances the degree of false positives destroys any value to the detection of the antigen as a diagnostic.

At the present state of the art, it is not necessary that the detection of the antigen in a physiological fluid be a perfect predictor of cancer. In many situations, where a tumor is removed, one can monitor a change in the presence in a physiological fluid of a specific epitopic marker as diagnostic of the effective removal of the tumor or the continued presence of the tumor. In other situations, two or more markers may be employed, providing for an enhanced certainty of the neoplastic condition. In other situations, such as imaging, it need only be that the marker is sufficiently more prevalent on the surface of the neoplastic cell as compared to the normal cell, so that the tumor may be distinguished.

It is therefore of great value to be able to define specific epitopes associated with tumors, which allow for diagnosis of neoplasia in physiological fluids, e.g. blood or serum, with a reasonable degree of accuracy, where the marker is used by itself or in conjunction with other markers.

2. Description of the Prior Art

Koprowski et al., Lancet (1982) i:1332–1333, reports the monoclonal antibody designated 19-9, related to diagnosing Lewis blood type as indicative of gastrointestinal cancer. The antibody reacts with approximately 60% of the sera from colon cancer patients. Magnani et al., *Cancer Res.* (1983) 43:5489–92, reported that the antigen to which 19-9 binds is a sialylated Lewis$^a$ structure or epitope that is present on mucins released into the sera of cancer patients. Bast et al., *N. Engl. J. Med.* (1983) 309:883–887, reports a monoclonal antibody that reacts with an antigen, designated CA125, which is a high molecular weight glycoprotein and is found in 82% of the sera of patients with ovarian carcinoma. Rauvala, *J. Biol. Chem.* (1976) 251:7517–7520, reports the sialylated derivative of lacto-N-fucopentaose III as a novel ganglioside of human kidney, which is called sialylated Le$^x$.

The significance of sialylation in neoplasma has been the subject of many reports. See, for example, Warren et al., *Proc. Natl. Acad. Sci. USA* (1972) 69:1838–1842; Van Beek et al., *Br. J. Cancer* (1977) 36:157–165; Warren et al., *Biochem. Biophys. Acta* (1978) 516:97–127; Glick, *Biochemistry* (1979) 18:2525–2532; and Yogeeswaran and Tao, *Biochem. Biophys. Res. Commun.* (1980) 95:1452–1460. Many monoclonal antibodies raised against cancer cells have been reported as having their main activity against terminal carbohydrate structures such as sialylated Lewis$^a$ (Magnani et al., *J. Biol. Chem.* (1982) 257:14365–14369); Lewis$^b$ (Brockhaus et al., ibid (1981) 256:13223–13225); and Lewis$^x$ (Hakomori et al., *Biochem. Biophys. Res. Commun.* (1981) 100:1578–1586).

SUMMARY OF THE INVENTION

The detection of molecules containing sialylated Le$^x$ epitope or structure in sera is employed as a diagnostic. Monoclonal antibodies to sialylated Le$^x$ (structure) find use in a variety of applications, both in vitro and in vivo in diagnosis and therapy. The hybridoma producing the monoclonal antibody can be used for transforming other cells to make them monoclonal antibody producing or as a source of the gene for expression of the immunoglobulin.

DESCRIPTION OF THE SPECIFIC EMBODIMENTS

Novel methods and compositions are provided concerned with the detection of the presence of an epitope having the following structure

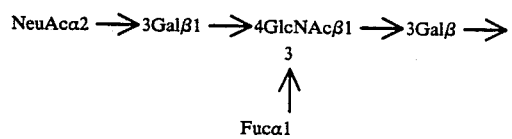

and/or binding to the monoclonal antibody designated CSLEX1. The epitope is found to be present with a high incidence on neoplastic cells, as well as a significant number of normal tissues.

The epitope is characterized by being a sialylated form of the Lewis$^x$ structure. It is generally found on granulocytes, as determined by cytotoxicity with the CSLEX1 antibody, but is not found associated with lymphocytes, monocytes, platelets and red blood cells, as evidenced by the same cytotoxic test. It is also not evident on most leukemia-lymphoma lines.

The sialylated Le$^x$ epitope may be found in normal tissue and the glands and mucosa of esophagus, limited parts of some pancreatic acinar cells and of deep crypts of colon, and the proximal tubules and descending loops of Henle. The antigen is not detected in the stomach, lung, brain, thymus, skin, ovary, uterus, adrenal glands, and muscle of the normal tissue tested.

The sialylated Le$^x$ epitope is present on numerous carcinomas, including adenocarcinomas of the stomach, colon, and pancreas, as well as such tumors as esophagus, breast and ovary.

The epitope is also found on the precursor cells to granulocytes, as evidenced by the effect of the CSLEX1 antibody on CFU-C.

The sialylated Le$^x$ structure, as sialosyl lactofucopentaosyl (III) ceramide and sialosyldifucosyl ganglioside (VIB) can be detected and distinguished from numerous other gangliosides, ceramides and globosides.

The sialylated Le$^x$ structure has been detected on a glycolipid present in the human kidney (Rauvala, *J. Biol. Chem.* (1976) 251:7517–7520) and is probably present on mucins as evidenced by the partial reduction of activity by pronase and its presence in the luminal content of tubules in colon adenocarcinomas.

The sialylated form of Le$^x$ can be used in a wide variety of ways. It can be used as a hapten conjugated to an antigen to provide an immunogen for production of polyclonal antisera to sialylated Le$^x$ or preferably for monoclonal antibodies to sialylated Le$^x$. The antibodies may be IgM, IgG, or IgA, particularly IgM or IgG. The antibodies may be cytotoxic or noncytotoxic in combination with complement or other lysing activity present in blood.

The sialylated Le$^x$ may be modified for use as a reagent in diagnostic assays. That is, the hapten may be conjugated, covalently or non-covalently through receptors, e.g., antibodies, to labels which provide for a detectable signal. Illustrative labels include radioisotopes, e.g., $^3$H, $^{125}$I, $^{131}$I; fluorescers, e.g., fluorescein, phycobiliproteins, rare earth chelates, dansyl, rhodamine, etc.; enzyme substrates and inhibitors; enzymes, such as horseradish peroxidase, glucose oxidase, glucose-6-phosphate dehydrogenase, acetylcholinesterase, etc.; particles, e.g., dextran, agarose, metal particles, magnetic particles, polystyrene particles, etc. or the like. Methods for conjugating haptens to the various labels have been extensively described in the literature, see, for example, U.S. Pat. Nos. 3,817,837; 4,134,792; and 4,220,722. The site of linkage need not be sialylated lacto-N-fucopentaose III, but may be bonded through a group attached to the Le$^x$ antigen, such as a phospholipid, linking group, or the like.

As already indicated, the hapten can be conjugated to an antigen to provide an immunogen which will elicit antibodies. Alternatively, cells carrying the hapten can be employed, either intact or as fragments, for eliciting an immune response in an appropriate vertebrate. Particularly, it will be desirable to produce monoclonal antibodies specific for the hapten in accordance with conventional techniques (Köhler and Milstein, *Nature* (1975) 256:495-497). While any species can be used for preparing monoclonal antibodies, for the most part mice will be employed, as being the most convenient and having useful fusion partners available. However, for use in therapy in humans or in vivo imaging in humans, it may be desirable to prepare human monoclonal antibodies. Illustrative human fusion partners may be found in application Ser. No. 247,652, filed Mar. 26, 1981, now U.S. Pat. No. 4,451,570 and European patent application No. 0 044 722, published Jan. 27, 1982. The techniques for immunizing the host, fusing, cloning, selecting and isolating monoclonal antibodies is well established and need not be further described here. For that purpose, the above-cited references are incorporated by reference.

The monoclonal antibodies may find use in diagnosis, therapy, in vivo imaging, or the like. Depending upon the particular use, the antibodies may be used by themselves or in combination with other materials, conjugated covalently or non-covalently to the antibodies. The same types of labels which were described for use with the hapten may be employed with the antibodies for use in diagnostic assays. For in vitro imaging, radionuclides other than those described will be employed, particularly technetium, iodine, or the like.

The labeling employed will follow conventional techniques and the number of labels per antibody will vary depending upon the nature of the label, the sensitivity of the signal desired, the purpose of the labeling, and the like. The monoclonal antibodies may be used in a wide variety of diagnostic assays for detection of molecules with the sialylated Le$^x$ hapten in blood, serum or plasma. Numerous assays have been developed for use with antibodies for the detection of a wide variety of haptens, which would be applicable here. See the U.S. Patents cited above.

The hybridomas which are prepared can be used in a variety of ways, for example, for fusion with other fusion partners to provide for new hybridomas making the desired antibodies, as a source of the genes coding for the particular antibody, for use in developing the production of the antibodies by other than the hybridomas, or for use as reagents, where the binding sites of the hybridoma may be used in an assay.

The entire antibody need not be used, but rather only fragments, such as Fab, (Fab')$_2$, Fv, or the like.

Of particular interest is the murine monoclonal IgM designated CSLEX1.

The following examples are offered by way of illustration and not by way of limitation.

EXPERIMENTAL

Methods and Materials

Immunization and Somatic Cell Hybridization

Four- to six-week old female BALB/c mice were immunized subcutaneously with a 0.5 mg membrane protein from stomach adenocarcinoma tissue (32-OP-T-ST) emulsified in complete Freund's adjuvant. Two booster injections with the same amounts of membrane protein were given at two-week intervals. After three days, fusion of spleen cells was done with myeloma P3-X63-Ag8.653 (Kearney et al., *J. Immunol.* (1979) 123:1548-1550) by a modified method of Kohler and Milstein employing Percoll gradient concentration of spleen blast cells. Two weeks after fusion, supernatants were analyzed for antibody production by ELISA and a microcytotoxicity test. One hundred thirty-eight macroscopic clones were identified after fusion, 17 of which were reactive with the immunizing tissue but not with normal stomach and colon. This hybrid clone was subcloned twice by limiting dilution and passaged into BALB/c mice to produce ascites.

Tissues. Human tumor tissues from various organs were obtained at surgery and stored at −80° C. Normal human tissue was obtained from cadaver kidney donors and from patients at autopsy with no neoplastic disease, then immediately frozen in a mixture of isopentane dry ice and stored at −80° C.

Cell lines. Stomach cancer cell line (MKN1, MKN28, MKN45 and MKN74 established by Dr. H. Hojo and KATO-III established by Dr. M. Sekiguchi) were obtained from the First Department of Pathology in Niigata University (Prof. H. Watanabe), Japan. Stomach cancer line MK-92 was established by Drs. S. Mukai and Y. Kurosu (Nippon University, Japan). Lung and colon cancer lines (PC-1, PC-3, PC-6, PC-7, PC-8, PC-9, PC-10, PC-12, PC-13, PC-14, QG-56, and C-1) were obtained from Dr. Y. Hayata (Tokyo Medical College, Japan) and Dr. K. Tanaka (Kyushu University, Japan). Colon cell line M-7609 was obtained from Dr. M. Fukushima (Hirosaki University, Japan). Esophagus cancer line (TE-1 and SH1) were established by Dr. T. Nishihira (Tohoku University, Japan) and Dr. Iizuka (National Cancer Center, Japan). Other cell lines employed in this study were obtained from the American Type Culture Collection. All cell lines were maintained in culture in RPMI-1640 medium supplemented with 15% fetal calf serum (FCS), penicillin and streptomycin.

Membrane preparation. Crude membrane fraction was isolated from frozen tissues. Briefly, specimens were thawed in PBS at 4° C., pH 7.4, containing 1mM phenylmethylsulfonyl fluoride (PMSF), and 2mM CaCl$_2$. After mincing, cells were disrupted in an N$_2$ cell-disruption bomb followed by differential centrifugation of the disrupted cells. The crude membrane fraction was resuspended in PBS and stored at −80° C.

Monoclonal Antibody Screening by ELISA

For the micro-ELISA testing, Terasaki tissue culture plates (Falcon) were coated with various membrane fractions (at 25 μg/ml in bicarbonate buffer, pH 9.6) overnight at 4° C. After washing in PBS-0.05% Tween 20 TM, the wells were coated with 1% ovalbumin in bicarbonate buffer for 1 hr at 37° C. Following removal of the ovalbumin, 5 μl of sample were added and incubated for 2 hr at 37° C. After washing 3 times (with PBS-0.05% Tween 20 TM), 5 μl of peroxidase-labeled goat antimouse Ig (IgG+IgM) (KPL Laboratories) were allowed to react for 1 hr at 37° C. After washing 5 times, 5 μl of o-phenylenediamine were added at room temperature for 15 min. The reaction was stopped with 2.5 M sulfuric acid. The optical density was measured at 492 nm with a Dynatech TR200 reader.

Microcytotoxicity Test

The complement-dependent microcytotoxicity test was performed according to standard microtechniques (Terasaki et al, *Am. J. Clin. Pathol.* (1978) 69:103–120). Briefly, 1 μl of antibody was incubated with approximately 1500 target cells for 30 min followed by 1 hr incubation with rabbit complement at 25° C. Viability was assessed by dye exclusion.

Indirect Immunofluorescent Assay

Indirect immunofluorescence was performed by reacting cells with 50 μl of appropriately diluted antibodies at room temperature for 30 min. After washing 3 times with PBS-0.01% sodium azide, the cells were incubated in 50 μl of FITC-conjugated goat antimouse IgM for another 30 min at 4° C., followed by washing 3 times. The cells were examined by fluorescence microscopy 10~20 μg/ml mouse myeloma IgM were used as negative controls.

Immunoperoxidase Staining

Normal and neoplastic fresh tissues were used to examine immunochemical localization of the reactive antigens by immunoperoxidase staining. Cryostat-prepared tissue sections fixed in 4% formalin in Tris-buffered solution (TBS) for 1.5 to 5 min were incubated with monoclonal antibodies diluted in TBS with 1% bovine serum albumin (BSA) for 1 hr at room temperature. Five to ten μg/ml mouse myeloma IgM were used as negative controls. After washing in PBS, peroxidase conjugated F(ab')2 of goat antimouse IgG+IgM (KPL Laboratories) diluted 1:100 was added to the tissue section for 45 min at room temperature. After washing in PBS, the slides were treated for 6 min in 0.021% w/v 3-amino-9-ethylcarbozole (Sigma Chemical) in 0.02 M sodium acetate buffer at pH 5.2 and 0.01% $H_2O_2$, then counterstained with hematoxylin, and mounted in glycerol/PBS.

Determination of the Nature of the Epitope

To determine whether the epitope is based on sugar or protein, the tissue was treated with either proteolytic enzymes to remove activity based on protein or neuraminidase to remove activity based on sugar. The treated tissue was then analyzed for the presence of the epitope by ELISA or by immunoperoxidase staining. The immunizing stomach adenocarcinoma tissue was enzymatically treated using pronase (60 μg/0.1 ml, Calbiochem-Behring, San Diego, Calif.), trypsin (500 μg/0.1 ml, Worthington Biochemical, Freehold, N.J.), ficin (10 μg/0.1 ml. Sigma Chemical, St. Louis, Mo.) or neuraminidase (0.5 Iul/ml, 0.1 Iu/ml, 0.02 Iu/ml, from V. chores, Calbiochem). Those enzymatic reactions were performed at 37° C. for one hour. Following the enzymatic reaction, an ELISA was performed using the enzyme peroxidase and 5 mM sodium periodate incubated at 4° C. for one hour.

Neuraminidase treatment was additionally performed using neuraminidase from *Arthrobactor ureafaciens* incubated at 37° C. for periods of two hours. Those neuraminidase treated tissues were subsequently stained using immunoperoxidase as described above.

CFU-C Assay (Colony Forming unit-complement)

For CFU-C assay, 50 μl of bone marrow cell suspension at $3\times10^6$/ml in RPMI 1640 medium containing 10% FCS was incubated with 25 μl of various dilutions of monoclonal antibody at 37° C. for 30 min. Normal rabbit serum was added as a complement source and the incubation continued for 60 min. The treated cells ($1\times10^5$) were mixed with alpha medium containing 20% FCS, 20% PHA-LCM(phytohemagglutinin), and 0.3% agar, and then placed onto a microplate. After ten days' incubation at 37° C. in 5% $CO_2$ air, the number of colonies with more than 40 cells per colony were counted. The results were expressed as percent recovery of colony forming cells relative to controls.

Solid Phase Radioimmunoassay

Determination was made according to the procedure described by Kannagi et al., *Cancer Res.* (1983) 43:4997–5005. Each well was coated with 10 ng of glycolipid together with 50 ng lecithin and 30 ng of chloresterol. Structures of the various glycolipids used in this solid phase radioimmunoassay, as well as those used in the TLC immunostaining assay described below, are shown in Table 6.

TLC Immunostaining

TLC immunostaining was done on a Baker's HPTLC mini-plate (5×6 cm) using the method of Magnani et al., *Anal. Biochem.* (1980) 109:399–402. Antibody was diluted 300 times and applied on a TLC plate in order to minimize nonspecific staining.

Results

Reactivity Against Normal Peripheral Blood Cells and Leukemia-Lymphoma Lines The CSLEX1 monoclonal antibody was tested from cytotoxicity activity with normal panel cells and leukemia-lymphoma lines as shown below in Table 1.

TABLE 1

Cytotoxicity of Monoclonal Antibody CSLEX1 Against Normal Panel Cells and Leukemia/Lymphoma Lines

| Cells Tested | No. of Tested Cells | No. of Positive | Reciprocal Titer |
|---|---|---|---|
| T lymphocytes | 110 | 0 | |
| B lymphocytes | 55 | 0 | |
| Monocytes | 21 | 0 | |
| Granulocytes | 20 | 20 | 1:10⁴ |
| Platelets | 15 | 0 | |
| RBC: | | | |
| A | Pooled | 0 | |
| B | Pooled | 0 | |
| O | 8 | 0 | |

TABLE 1-continued

Cytotoxicity of Monoclonal Antibody CSLEX1 Against
Normal Panel Cells and Leukemia/Lymphoma Lines

| Cells Tested | No. of Tested Cells | No. of Positive | Reciprocal Titer |
|---|---|---|---|
| T-ALL lines<br>8402, CEM, MOLT-4, HPB-MLT | 4 | 0 | |
| B-lymphoma lines<br>Daudi, Ramos, Raji, Wel | 4 | 0 | |
| CALL lines<br>KM-3, Reh | 2 | 0 | |
| APL line<br>HL-60 | 1 | 1 | $1:10^4-10^5$ |
| Histiocytic lymphoma line<br>U-937 | 1 | 1 | $1:10^4-10^5$ |

The IgM antibody (ascites titer $1:10^4$) was cytotoxic to granulocytes and non-cytotoxic against lymphocytes, monocytes, platelets, and red blood cells tested. In leukemia-lymphoma lines it was reactive to only two cell lines, APL line (HL-60) and histiocytic lymphoma line (U-937), but not to T-ALL lines (8402, CEM, MOLT-4, HPB-MLT), B-lymphoma lines (Daudi, Ramos, Raji, Wel), and CALL lines (KM-3, Reh) examined. The immunofluorescence of CSLEX1 against these leukemia-lymphoma lines yielded identical results.

Reactivity Against Various Solid Tumor Cell Lines

Thirty-four various tumor cell lines were examined for reactivity by microcytotoxicity, immunofluorescence, and immunoperoxidase staining as shown below in Table 2. CSLEX1 yielded positive results with two stomach carcinoma lines (KATO-III and MKN28), one lung adenocarcinoma line (PC-3), three lung squamous cell carcinoma lines (PC-1, PC-9, QG-56), five colon adenocarcinoma lines (C-1, M7609, COLO 205, WiDr, COLO 320), two breast carcinoma lines (SK-BR-2 III and BT-20), and one esophagus tumor line (TE-1). A total of 14 of 34 cell lines (41%) showed a positive reaction. An especially high frequency of positive reactivity was observed in the colon adenocarcinoma lines (five of seven or 71%).

TABLE 2

Reactivity of Monoclonal Antibody CSLEX1 Against Solid Tumor Cell Lines by Cytotoxicity/Immunofluorescence/Immunoperoxidase

| Cell Line | Origin | Cytotoxicity | Immuno-fluorescence | Immuno-peroxidase |
|---|---|---|---|---|
| Stomach | | | | |
| KATO-III | Signet ring cell carcinoma | + $(1:10^4)$** | + | + |
| MKN28 | Adenocarcinoma (well)*** | N.T.* | + | + |
| MKN1 | Adenosquamous cell carcinoma | N.T. | − | − |
| MKN45 | Adenocarcinoma (poor) | − | − | − |
| MKN74 | Adenocarcinoma (well) | − | − | − |
| MK-92 | Signet ring cell carcinoma | − | − | − |
| Lung | | | | |
| PC-1 | Squamous cell carcinoma (poor) | N.T. | + | + |
| PC-3 | Adenocarcinoma (mod) | N.T. | + | + |
| PC-6 | Small cell carcinoma | − | − | − |
| PC-7 | Adenocarcinoma (poor) | − | − | − |
| PC-8 | Adenocarcinoma (poor) | − | − | − |
| PC-9 | Squamous cell carcinoma (well) | + $(1:10^5)$ | + | + |
| PC-10 | Squamous cell carcinoma (mod) | − | − | − |
| PC-12 | Adenocarcinoma (well) | − | − | − |
| PC-13 | Large cell carcinoma | − | − | − |
| PC-14 | Adenocarcinoma (poor) | − | − | − |
| QG-56 | Squamous cell carcinoma | ± $(1:10^4)$ | + | + |
| A-549 | Lung carcinoma | − | − | − |
| SK-LU-1 | Adenocarcinoma (poor) | − | − | − |
| Colon | | | | |
| C-1 | Adenocarcinoma (poor) | N.T. | + | + |
| M-7609 | Adenocarcinoma (poor) | ± $(1:10^4)$ | + | + |
| S-7512 | Simple cancer | − | − | − |
| COLO 205 | Adenocarcinoma | + $(1:10^4)$ | + | + |
| WiDr | Adenocarcinoma | ± $(1:10^4)$ | ± | +~± |
| SK-CO-1 | Adenocarcinoma | N.T. | + | + |
| COLO 320 | Adenocarcinoma | − | − | − |
| Breast | | | | |
| SK-BR-1 III | Adenocarcinoma | − | − | − |
| SK-BR-2 III | Adenocarcinoma | + $(1:10^5)$ | + | + |
| BT-20 | Adenocarcinoma | + $(1:10^4)$ | + | + |
| Esophagus | | | | |
| TE-1 | Squamous cell carcinoma (well) | N.T. | + | + |
| SH-1 | Squamous cell carcinoma | − | − | − |
| Liver | | | | |
| SK-HEP-1 | Adenocarcinoma | − | − | − |
| Bladder | | | | |
| J82 | Transitional cell carcinoma (poor) | − | − | − |
| SCaBER | Squamous cell carcinoma | − | − | − |

*N.T. = not tested; ** = reciprocal titer; + = moderately or strongly positive; ± = weakly positive; − = negative;
***well = well differentiated; mod = moderately differentiated; poor = poorly differentiated Tissue Distribution of the CSLEX1 Antigen in Normal and Malignant Tissues The tissue distribution of CSLEX1 antibody reactive antigen by immunoperoxidase staining is given in Table 3. Strong positive staining of normal tissues was observed in the glands and mucosa of esophagus, as well as in the proximal tubules and descending loops of Henle of the kidney. Weaker staining was observed in very limited parts of some deep crypts of the colon, in some acinar cells of the pancreas, hepatic cells and Kupffer cells in the liver, and granulocytes. The antigen was not detected in the stomach, lung (except alveolar macrophage), brain, thymus, skin, ovary, uterus, adrenal gland, muscle, or connective tissues examined.

Seventy-four various tumor tissues tested are shown in Table 4. Surprisingly, the antigen recognized by CSLEX1 antibody could be detected in many carcinomas - 16 of 17 stomach adenocarcinomas, 13 of 17 colon adenocarcinomas, 10 of 16 lung tumors, 2 of 4 esophagus tumors, 3 of 3 pancreas adenocarcinomas, 2 of 8 breast tumors, and 3 of 6 ovary tumors. Mouse myeloma IgM (5-10 μg/ml) was used as a control and did not react with any of these tissues. All samples contained only tumor tissue, except for 6 (of 17) colon adenocarcinoma samples, which contained both tumor tissue and adjacent normal tissue. In 5 of these 6 samples, the normal tissue portions were not stained. Cancerous portions of the positively-reacting colon adenocarcinoma samples showed staining in the apical cytoplasm of the cancer tubules and in the luminal contents. Three of 4 stomach and 8 of 8 colon samples containing mucin lakes showed positive reactivity with this antibody, probably due to the presence of antigen on mucin. A high frequency of positive staining of tumor tissues by CSLEX1 was observed in adenocarcinomas such as stomach, colon, and lung without regard to differentiating grade of the cancer cells. Positive staining was also observed in some squamous cell carcinoma samples. The CSLEX1 antibody reacted with 50 of 74 (68%) tumors tested.

TABLE 3

Tissue Distribution of the CSLEX1 Antigen in Normal Tissue

| Tissue | Reactivity |
|---|---|
| Hematopoetic/Lymphoid Organ | |
| RBC | − |
| Granulocyte | +[b] |
| Lymphocyte | − |
| Thymus (3)[a] | − |
| Spleen (4) | ± PMNs and reticulocytes |
| Kupffer cell (6) | ± |
| Nervous System | |
| Brain (2) | − |
| Plexus | − |
| Peripheral nerve | − |
| Digestive System | |
| Esophagus (4) | ++ mucosa and esophageal glands |
| Stomach (12) | − |
| Colon (11) | ± limited parts of some deep crypts |
| Liver (6) | ± hepatic cells |
| Pancreas (8) | ± some parts of acinar cells |
| Bile duct (6) | − |
| Pancreas duct (8) | − |
| Urinary Tract | |
| Kidney (8) | ++ proximal tubules and descending loops of Henle |
| Ureter | + epithelium |
| Lung (6) | |
| Alveolar Mφ | ± |
| Parenchymal cell | − |
| Bronchi | − |
| Skin (1) | |
| Epidermis | − |
| Connective tissue | − |
| Sweat gland | − |
| Vascular System | |
| Artery | − |
| Vein | − |
| Others | |
| Ovary (1) | − |
| Uterus (1) | − |
| Adrenal glands (1) | − |
| Muscle | − |

[a]Number of samples tested
[b]For scoring of slides, see "Materials and Methods"

TABLE 4

Reactivity of the CSLEX1 Antibody Against Tumor Tissues

| Cancer | No. Tested | % Positive | Reactivity[a] +++ | ++ | + | ± | Mucin[b] |
|---|---|---|---|---|---|---|---|
| Stomach | 17 | 94% | 8 | 1 | 4 | 3 | 3/4 |
| Colon | 17 | 76% | 2 | 1 | 6 | 6 | 8/8 |
| Lung: | | | | | | | |
| AD[c] | 9 | 78% | 5 | 1 | 0 | 1 | |
| SQ | 4 | 50% | 1 | 0 | 1 | 0 | |
| UC | 3 | 33% | 0 | 0 | 0 | 1 | |
| Total | 16 | 63% | 6 | 1 | 1 | 2 | |
| Esophagus | 4 | 50% | 0 | 2 | 0 | 0 | |
| Ovary | 6 | 50% | 3 | 0 | 0 | 0 | |
| Breast | 8 | 25% | 0 | 1 | 0 | 1 | |
| Bladder | 1 | 100% | 1 | 0 | 0 | 0 | |
| Kidney | 1 | 0% | 0 | 0 | 0 | 0 | |
| Pancreas | 3 | 100% | 1 | 1 | 0 | 1 | |
| Uterus | 1 | 0% | 0 | 0 | 0 | 0 | |
| Total | 74 | 68% | | | | | |

[a]Reactivity +++, diffuse; ++, 40-80%; +, 10-40%; ± 1-10%.
[b]No. of positive/No. of tested samples containing mucin lakes.
[c]AD, adenocarcinoma; SQ, squamous cell carcinoma; UC, undifferentiated carcinoma.

Enzyme Treatment of CSLEX1 Reactive Antigens

Treatment of the immunizing stomach adenocarcinoma with neuraminidase and sodium periodate completely dimished binding of CSLEX1. Treatment with pronase partly decreased binding (Table 5-A). These results suggest that the antigen on the immunizing tissue may be a sialylated glycoprotein.

Immunoperoxidase staining of normal kidney tubules and esophagus tissue with CSLEX1 was abolished by neuraminidase treatment (Table 5-B). Antigens detected by antibody (CLEX1) directed against Le$^x$ were not affected by neuraminidase treatment.

TABLE 5

Effect of Enzyme Treatment (A) ELISA of CSLEX1 with Enzyme-Treated Immunizing Tissue

| | Control | Pronase | Trypsin | Ficin | NaIO$_4$ | Neuraminidase[a] (units) 0.5 | 0.1 | 0.02 |
|---|---|---|---|---|---|---|---|---|
| O.D. | 1.5 | 0.42 | 0.88 | 1.39 | 0.10 | 0.14 | 0.17 | 0.35 |

(B) Effect of Neuraminidase on the Expression of CSLEX1-reactive Antigens by Immunoperoxidase Assay

| Tissue Tested | Monoclonal Antibody | Neuraminidase[c] Treatment (units) 0.5 | 0.1 | 0.01 | PBS |
|---|---|---|---|---|---|
| (1) Kidney (1KD580) | CSLEX1 | − | − | ±[d] | ++ |
| | CLEX1 | ++ | ++ | ++ | ++ |
| | Mouse myeloma IgM | − | − | − | − |
| (2) Esophagus (1ES390) | CSLEX1 | − | − | ± | ++ |
| | CLEX1 | ++ | ++ | ++ | ++ |

TABLE 5-continued

Effect of Enzyme Treatment

| | | | | |
|---|---|---|---|---|
| Mouse myeloma IgM | − | − | − | − |

*Antibody dilution 1:800
*[a]Neuraminidase from *Vibrio choleae* (Calbiochem)
*Negative <0.2 at O.D.$_{492}$
*[c]Neuraminidase from *Arthrobactor ureafaciens* (Calbiochem)
*[d]For scoring of slides, see "Materials and Methods"

oside, but with neither the sialosyl Le$^a$ fraction or other gangliosides.

Table 6 shows the fucogangliosides that were tested against the CSLEX1 antibody. It can be seen that the monoclonal antibody reacted with the first two gangliosides, which contain the sialosyl Lewis$^x$ hapten. The antibody did not react with similar derivatives having chemical structures which were slightly different as shown below in Table 6.

TABLE 6

Structures of Novel Fucogangliosides and Their Reactivity with the CSLEX1 Monoclonal Antibody

| | | Reactivity |
|---|---|---|
| 1. Sialosyldifucosyl-ganglioside (6B ganglioside) | 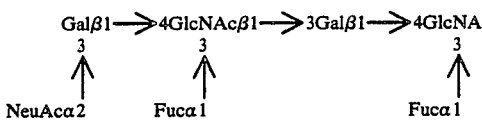 | ++ |
| 2. Sialosyllactofucopentaosyl (III) ceramide (Rauvala's ganglioside) | 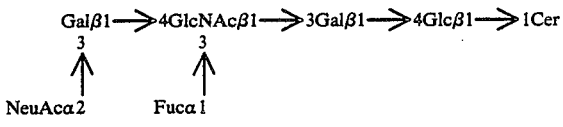 | ++ |
| 3. Sialosyl Le$^a$ | 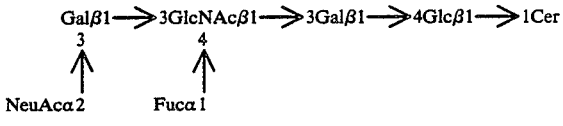 | − |
| 4. 6C ganglioside | 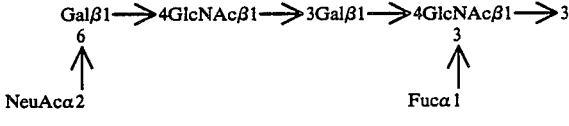 | − |
| 5. Difucosyllacto-nor hexasyloamide | 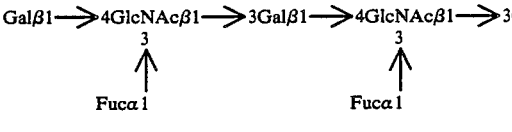 | − |
| 6. Sialosylparagloboside (SPG) | 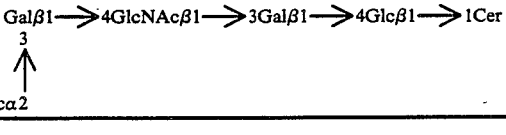 | − |

CFU-C Assay

The monoclonal antibody had an effect on CFU-C. The recovery of CFU-C was 28% at 1:10$^4$ dilution after treatment with rabbit complement. Control tests with an anti-Ia monoclonal antibody at a 1:10 dilution and rabbit complement yield 23% recovery. This indicates that CSLEX1 reacts with CFU-C, the precursor of granulocytes.

Reactivity of the CSLEX1 with Various Gangliosides

The reactivities with gangliosides at different antibody dilutions by solid phase immunoradioassay were determined. The antibody reacted with sialosyllactofucopentaosyl (III) ceramide (Rauvala) and sialosyldifucosylganglioside (6B), but not with others tested. The TLC immunostaining pattern of gangliosides with the CSLEX1 antibody was also determined. CSLEX1 reacted with both 6B ganglioside and Rauvala's gangli- Hemagglutination tests were performed in U-shaped wells containing 0.05 ml of two-fold dilutions of sera and 0.05 ml of 1% sensitized ox red blood cells. The reactions were read following 2 hr incubation at room temperature. Confirmation tests were performed by incubation with patient's sera and CSLEX1 before adding sensitized red blood cells. See Table 7.

The following data demonstrate that the CSLEX1 antibody reacts with the sera of 23% of 313 sera from cancer patients while not reacting with any sera from 80 normal persons. As in the case of sialylated Le$^a$, the sialylated form of Le$^x$ is present in cancer patients' serum but not in normal sera. (Magnani, Cancer Res. (1983) 43:5489-5492.) Thus, the CSLEX1 antibody can be used in diagnostic tests for detecting the existence of a tumor, monitoring the successful removal of a tumor and, furthermore, providing some indication of the locality of the tumor.

Although the foregoing invention has been described in some detail by way of illustration and example for purposes of clarity of understanding, it will be obvious that certain changes and modifications may be practiced within the scope of the appended claims.

TABLE 7

| Reverse Passive Hemagglutination Test With The CSLEX1 Monoclonal Antibody | | | | | | | | | | |
|---|---|---|---|---|---|---|---|---|---|---|
| Type of Disease | No. | % Pos. | 40 | 80 | 160 | 320 | 640 | 1280 | 2560 | 5120 |
| A. Malignant | | | | | | | | | | |
| Lung adenocarcinoma | 51 | 45 | 2 | 2 | 2 | 3 | 3 | 3 | 2 | 6 |
| Lung squamous cell carcinoma | 33 | 18 | 2 | 1 | 1 | 2 | | | | |
| Lung small cell carcinoma | 14 | 0 | | | | | | | | |
| Lung, other carcinoma | 14 | 14 | | | 1 | | | | 1 | |
| Stomach carcinoma | 56 | 20 | 4 | | | 2 | 2 | 1 | 1 | 1 |
| Colon carcinoma | 19 | 37 | | 1 | | 1 | 1 | 1 | 1 | 2 |
| Liver carcinoma | 21 | 5 | 1 | | | | | | | |
| Pancreas carcinoma | 6 | 33 | | | | | | 2 | | |
| Breast carcinoma | 29 | 38 | | 2 | | 2 | 1 | 1 | 2 | 3 |
| Others | 70 | 11 | 1 | 1 | | 1 | | 1 | | 4 |
| Total carcinomas | 313 | 23 | 10 | 7 | 4 | 11 | 7 | 9 | 7 | 16 |
| B. Benign | | | | | | | | | | |
| Ulcerative colitis | 38 | 0 | | | | | | | | |
| C. Normal Subjects | 80 | 0 | | | | | | | | |

What is claimed is:

1. A method for diagnosing a neoplastic condition in a human host suspected of having neoplasia, the method comprising:
   detecting the presence of sialylated $Le^x$ epitope containing compounds in blood.

2. A method according to claim 1, wherein a monoclonal antibody specific for sialylated $Le^x$ hapten is employed for said detection.

3. A method, for diagnosing a neoplastic condition in a human host suspected of having neoplasia, the method comprising:
   detecting the presence of sialylated $Le^x$ epitope containing compounds in blood, wherein a monoclonal antibody specific for sialylated $Le^x$ hapten is employed for said detection and said monoclonal antibody is CSLEX1 from hybridoma A.T.C C. accession no. HB 8580.

4. The murine hybridoma CSLEX1 having A.T.C.C. accession no. HB 8580.

5. A monoclonal antibody specific for sialylated $Le^x$ hapten, said antibody having substantially the binding characteristics of the monoclonal antibody CSLEX1, obtained from hybridoma having A.T.C.C. accession no. HB 8580.

6. A monoclonal antibody obtained from hybridoma CSLEX1 having the A T.C.C. accession no. HB 8580.

7. Sialylated $Le^x$ covalently bonded to a label capable of providing for a detectable signal.

8. Monoclonal antibody to sialylated $Le^x$ conjugated to a compound capable of providing a detectable signal, having substantially the binding specificity of monoclonal antibodies from hybridoma CSLEX1, A.T.C.C. accession no. HB 8580.

9. A monoclonal antibody according to claim 8, wherein said label is a fluorescer.

10. A monoclonal antibody according to claim 8, wherein said label is an enyzme.

11. A monoclonal antibody according to claim 8, wherein said label is a radioisotope.

* * * * *